(12) United States Patent
Haas

(10) Patent No.: US 8,969,095 B1
(45) Date of Patent: Mar. 3, 2015

(54) METHOD AND SYSTEM FOR EXPLOSIVE DETECTION

(76) Inventor: Jeffery S. Haas, San Ramon, CA (US)

( * ) Notice: Subject to any disclaimer, the term of this patent is extended or adjusted under 35 U.S.C. 154(b) by 874 days.

(21) Appl. No.: 13/066,922

(22) Filed: Apr. 28, 2011

(51) Int. Cl.
*G01N 33/00* (2006.01)
*G01N 31/22* (2006.01)

(52) U.S. Cl.
USPC ............. 436/164; 436/94; 436/109; 436/110; 436/155; 436/156; 422/50; 422/78; 422/530; 250/339.15; 250/458.1

(58) Field of Classification Search
USPC .................. 436/110, 109, 94, 155, 156, 164; 422/430, 78, 50, 530; 252/193; 250/458.1, 339.15
See application file for complete search history.

(56) References Cited

U.S. PATENT DOCUMENTS

| | | | |
|---|---|---|---|
| 4,788,039 A * | 11/1988 | Glattstein | 422/430 |
| 5,882,595 A * | 3/1999 | La Motte | 422/65 |
| 7,294,306 B2 | 11/2007 | Haas | |
| 7,867,445 B1 | 1/2011 | Haas | |
| 2005/0101027 A1 * | 5/2005 | Haas | 436/109 |
| 2007/0003435 A1 * | 1/2007 | Haas et al. | 422/58 |
| 2007/0202009 A1 * | 8/2007 | Nunes et al. | 422/58 |
| 2011/0057116 A1 * | 3/2011 | Trogler et al. | 250/458.1 |

OTHER PUBLICATIONS

U.S. Appl. No. 10/703,445, filed Jan. 11, 2011, Jeffery S. Haas.

* cited by examiner

*Primary Examiner* — Rebecca M Fritchman
(74) *Attorney, Agent, or Firm* — Dennis W. Beech

(57) ABSTRACT

The present invention is directed to methods and systems for detecting the presence of explosive elements. A sample element may be used to swipe an object for a test sample. The sample element may be positioned in a sample holder of a testing device having a heater. The heater may be programmed to heat the sample element and sample in a controlled manner through two or three temperature increases from approximately 35 degrees to 165 degrees centigrade in approximately 40 seconds. Prior to each temperature increase a first, second and third reagent fluid is applied to the sample holder, and during the temperature rise the sample holder is observed for the presence of various explosive elements by detecting colors as compared to a color chart. The color observations may be based on time and temperature variations using a testing device.

10 Claims, 4 Drawing Sheets

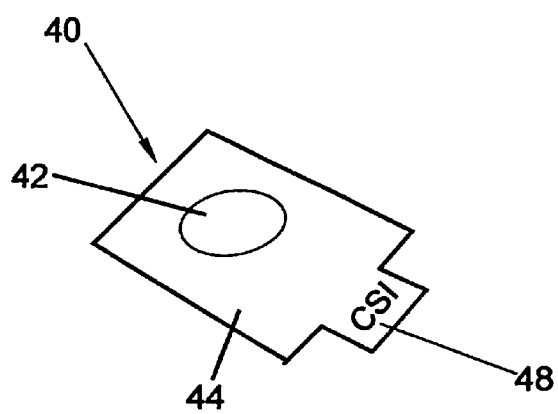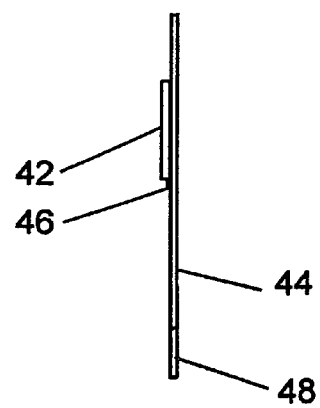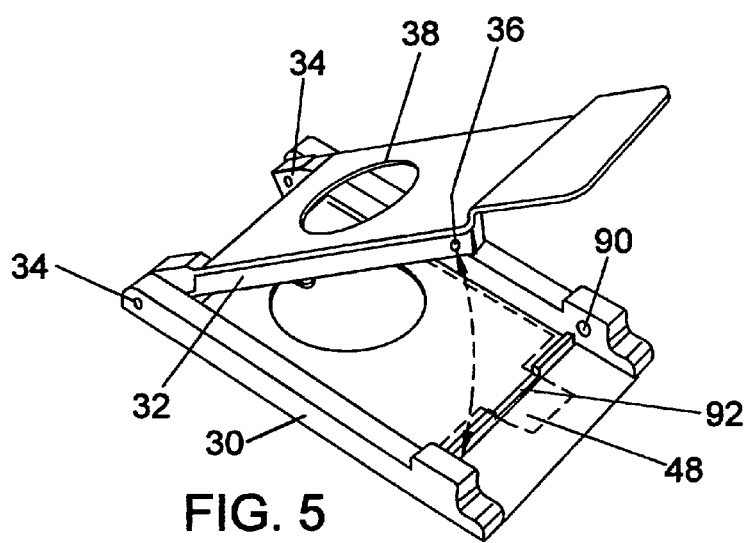

METHOD AND SYSTEM FOR EXPLOSIVE DETECTION

BACKGROUND OF THE INVENTION

This invention relates to systems and methods for detecting the presence of explosives and explosives residue. The new system and method may provide a compact test unit that incorporates a test method that may allow testing of sample articles at a selected location. The detection unit may use chemicals and other elements that reduce the hazard to a user.

Chemical detection of the presence of explosives and explosive residue has been known for many years. The methods and chemicals used in the past have tended to be cumbersome to transport and put into use at a selected site or location and the testing may have been time consuming. Special testing devices and apparatus may have been developed for specific explosives, but they may have been unreliable, dangerous to the user due to the chemicals used, or otherwise limited in identifying an explosives contaminated site or object.

A previously used chemical explosives identification technique that may have been reasonably reliable is thin layer chromatography or TLC. Testing apparatus and methods have been developed including kits for on-site testing. The colorimetric devices and methods including those using a TLC plate may have shortcomings for effective, efficient testing, e.g., difficulty of use, length of time, solvent waste disposal, use of toxic chemicals, large work area, need for calibration, limited type or number of explosive compounds detectable, use of glass as well as other issues.

The use of colorimetric testing or spot tests may have been recognized for many years as chemical reagents and methods were identified to detect the presence of a particular explosive. The colorimetric tests may afford quick results, may be easy to perform and may be sensitive relative to the explosive sample content, but may be limited in the number of different explosives detected. The most common spot test method may be to react explosives with a base, then allow time or heat the sample, then perform a Griess reaction test, and then allow more time or heat the sample. Various formulations of the Griess reagent may have been developed. Also numerous types of substrates, sorbent materials or swipes, such as, wool, cotton, polyfabrics, porcelain spot plates, TLC plates, corvettes, beakers, jars and the like may have been used to perform testing. All of these testing devices and methods may have been limited in the past as discussed above making them cumbersome and unwieldy to use and thereby limiting the flexibility necessary for quick, site selected and timely testing for detection of the presence of explosives or explosive residue.

Also various hand held devices that may have sample test pads attached to elongated rods, attached to test cards or otherwise structured as one time use and disposal may be disclosed in the literature. These devices general have simple squeeze or crush ampules with test solutions and rudimentary or no heating source for sample testing. Various of the disposable devices may actually be hazardous to a user if the sample and testing solutions are heated. The devices also may be prone to introducing errors in attempts to detect explosive material. More sophisticated time and temperature control testing is not compatible with these simple disposable testers.

SUMMARY OF THE INVENTION

The present invention is directed to methods and systems for detecting the presence of explosive elements. A sample element may be used to swipe an object for a test sample. The sample element may be positioned in a sample holder of a testing device having a heater. The heater may be programmed to heat the sample element and sample in a controlled manner through two or three temperature increases from approximately 35 degrees to 165 degrees centigrade in approximately 40 seconds. Prior to each temperature increase a first, second and third reagent fluid is applied to the sample holder, and during the temperature rise the sample holder is observed for the presence of various explosive elements by detecting colors as compared to a color chart. The color observations may be based on time and temperature variations using a testing device.

These and other features, aspects and advantages of the present invention will become better understood with reference to the following drawings, description and claims.

BRIEF DESCRIPTION OF THE DRAWINGS

FIG. 3 illustrates a top view of a sample element according to an embodiment of the invention;

FIG. 4 illustrates a side view of a sample element according to an embodiment of the invention;

FIG. 5 illustrates a perspective view of an open sample holder according to an embodiment of the invention;

DETAILED DESCRIPTION

The following detailed description includes the best currently contemplated modes for carrying out the invention. The description is not to be taken in a limiting sense, but is made merely for the purpose of illustrating the general principles of the invention.

Figure 1:
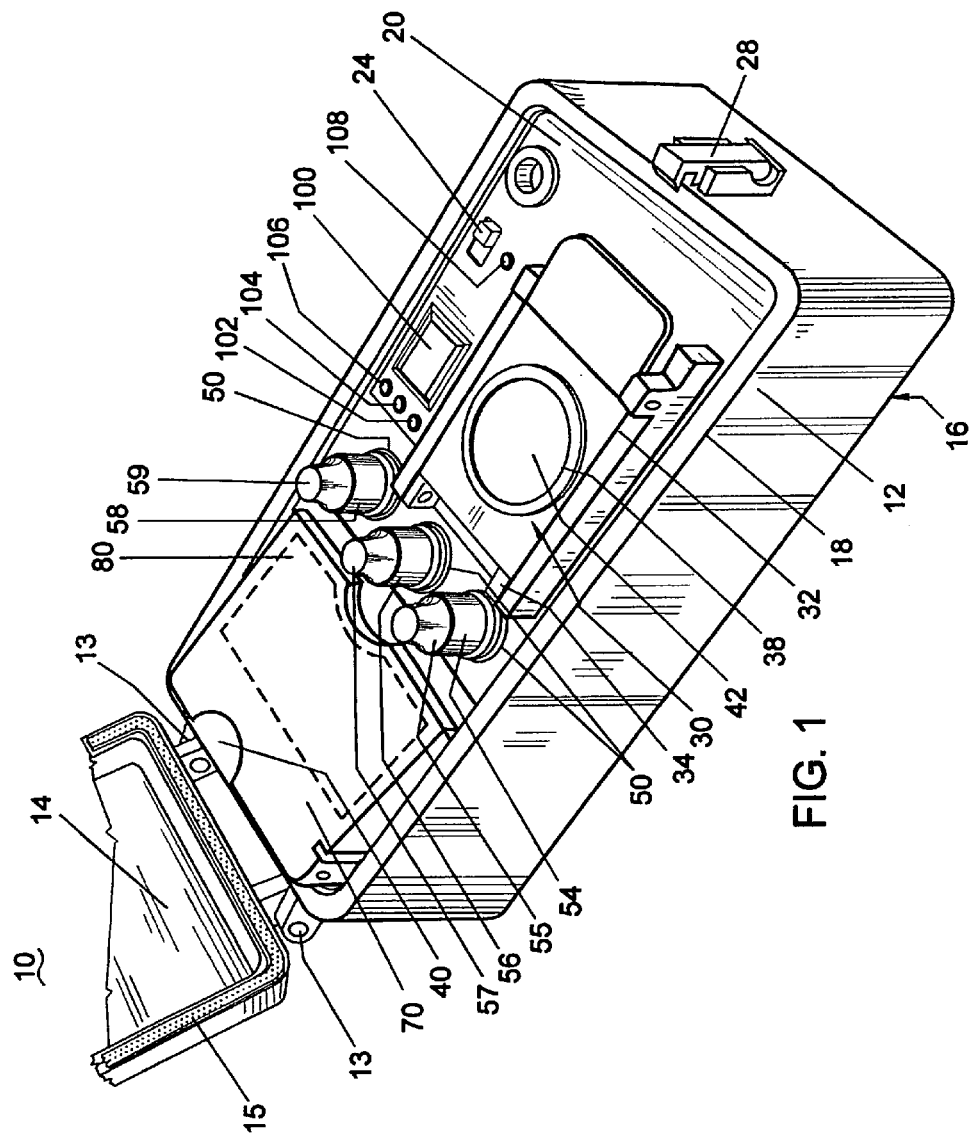
FIG. 1 illustrates a perspective view of a testing device with cover open according to an embodiment of the invention.
Figure 2:
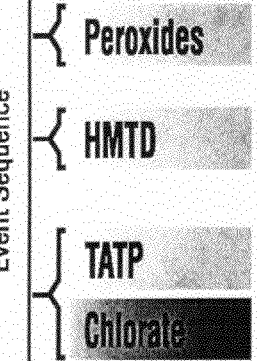
FIG. 2 illustrates a quick reference color chart according to an embodiment of the invention.
Figure 6:
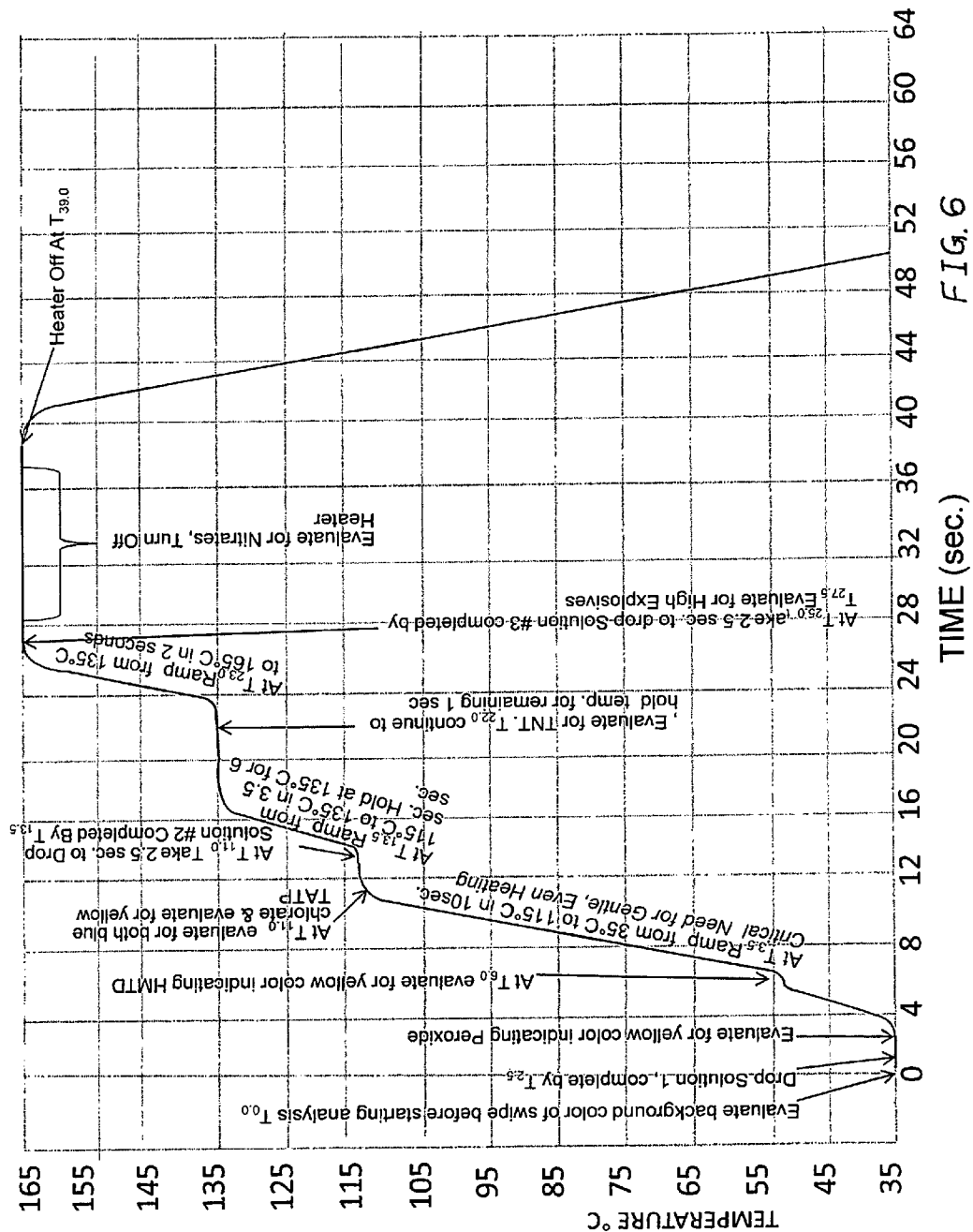
FIG. 6 illustrates a graph of the temperature versus time curve for an explosive test method according to an embodiment of the invention.

Referring to FIGS. 1 and 2, a colorimetric testing device 10 for various types of explosives and related energetic decomposition products, for example, peroxide, HMTD, TATP, chlorate, tetryl, nitro-, nitrato-, and nitramine-type explosives, all nitrate explosive such as black powders, mining gels, homemade explosives, gun propellants and other yet untested compositions may have a case 12 and cover 14 and may be easy to transport to a selected location for testing. Case 12 may have storage bin 70 for retaining extra swipes or swabs. The test device 10 may allow testing of explosive samples as low as a few nanograms to saturated milligram levels on a substrate swipe. Cover 14 or case 12 may be fitted with an O-ring or gasket 15 to seal against moisture or dirt. There may be a case latch 28 for retaining the closed cover 14 to the case 12.

The case 12 may have a bottom 16 assembled with an enclosure 18 having an upper panel 20. There may be enclosure attachments 26 such as screws, bolts, quick release devices or the like for access to the batteries 22. The case 12 may also be structured as a bottom wall with four side walls and a removable upper panel 20. The upper panel 20 may allow access to replace batteries or a separate, gasketed small plate in the side or bottom may be provided for battery access. The case 12 and cover 14 may be hinged or otherwise attached. Batteries 22 may be disposed in the case 12 with a power switch 24 positioned on the case 12 or on the upper panel 20 and a power on/off indicator 108. There may be a sample holder 30 attached to the upper panel 20 that may have a heater 60 disposed therein. The heater 60 may be positioned on a flexible heat resistant pad (not shown) and may be in communication with the batteries 22 and a temperature sensor 62. There may also be a voltage regulator 64 to allow use of an external power source.

Referring to FIGS. 1 through 5, there may be a sample retainer 32 attached by a hinge 34 to hold and clamp a sample element 40 or swipe. The sample retainer 32 may have a retainer aperture 38 and may be held in place by latch retainers 36. The sample element 40 may have a swipe pad 42 attached by pad attachment 46 to a backing element 44. The swipe pad 42 may be attached by adhesive, glue or other suitable element that maintains attachment and environment integrity up to approximately 165° C. without decomposing or other damage. The swipe pad 42 may be a defined size such as circular with an approximate diameter of 0.60 to 0.75 inches to accommodate test sample sizes, to not require excessive use of reagent fluid and to provide uniform flow of fluid. The pad attachment 46 may be chemically resistant and non-porous to inhibit the absorption of reagent fluid. The pad attachment, if for example adhesive, may also be of white color to not interfere with the visual evaluation of the swipe pad 42 during testing. If the pad attachment 46 is not positioned under the swipe pad 42, the backing element may be white colored in the area of the swipe pad 42. The pad attachment 46 may also be selected to minimize interference in heating swipe pad 42.

The swipe pad 42 may be formed of material that may be resistant to chemical degradation during testing in the approximate pH range of 1 through 14 to avoid reacting or decomposing. The swipe pad 42 may be white in color to aid test evaluation, may be heat resistant up to approximately 165° C. and may have hydrophilic properties for wetting using fluid reagents. The swipe pad 42 may also be roughened, for example, by use of a woven material, to aid in retrieving test sample particles from the environment. The swipe pad 42 may also be thick enough to resist damage such as tearing during sampling, yet not be too thick such that heating of the test sample is inhibited. When the sample element 40 may be positioned in the sample holder 30, the swipe pad 42 may be disposed relative to the retainer aperture 38.

Any geometric shape of swipe pad 42 may be used; however, a circular swipe pad 42 may provide for even wicking to the outer edges avoiding the occurrence of unwetted corners. It has been found by experiment that a swipe pad 42 circular shape with approximately 0.67 inch diameter and 0.001 inch to 0.003 inch thickness may allow an adequate test sample size of material to be wetted with a minimum use of reagent fluid. With a woven 100% continuous filament virgin polyester material, approximately 50 microliters of reagent may be sufficient for testing. Selecting swipe pad 42 characteristics may provide adequate surface area to perform the test sample collection or swiping task and reduce the volume of reagent necessary for transport with the testing device 10.

The backing element 44 may support the swipe pad 42 when in use for example to collect test samples. It may also protect the swipe pad 42 from contamination due to handling and may protect the swipe pad 42 from the heater 60. It has been found by experiment that a polyester material such as MYLAR may be used for the backing element 44. The polyester material may be resistant to chemical degradation and it may facilitate heat transfer to the swipe pad 42 without decomposing due to heating. The polyester material may be white in color to aid in test evaluation. The sample element 40 may have a tab 48 with identifying markings, for example, CSI, for a user to orient the sample element 40 when placing it in the sample holder 30. The sample element 40 may also have a hole or cross slit 94 for positioning on a protruding element 92 located on the holder plate 90, which may be termed a lock and key, to aid in proper positioning of the sample element 40 in the sample holder 30. The sample element 40 may be producible in elongated sheets and be flexible to be rolled in quantities for storage and transport in the storage bin 70. The peripheral shape of the sample element 40 and the wall of sample holder 30 may also serve to properly position the sample element 40.

There may be three cavities 50, for positioning fluid containers 54, 56, 58 in the case 12. The fluid container 54 may have cap 55, the fluid container 56 may have cap 57, and the fluid container 58 may have cap 59. The fluid containers 54, 56, 58 may have a reagent for use in testing a test sample for the presence of explosives or residues thereof. The fluid containers 54, 56, 58 may be one of various types, for example, squeeze to release a specific volume drop of fluid, have a dropper incorporated in the cap, have a pump or pump type cap to move fluid, or other fluid extraction method or structure.

A first reagent test may use a first reagent fluid that may have a titanium metal oxide salt complex and aniline or aniline derivative dissolved in a water and ethanol mixture at low pH and may be used in a first reagent test to impart a color to peroxide, peroxy-compounds such as HMTD and TATP, and chlorate. The ethanol and water may also have minimum nitrite content to avoid reaction to successive type reagent tests that may give false positive results. For example, if a 10 nanogram detection threshold may be used any nitrite content in the solutions may be less than 0.2 nanograms per microliter of fluid to minimize corruption of test results or false detection. The first reagent fluid is used with a heat ramp over time profile to sequentially evolve color reactions to peroxide, peroxy-compounds such as HMTD and TATP, and chlorate.

The first reagent test may use a first reagent fluid that may have an optimum detection performance range with the fluid having a titanium metal oxide salt complex and aniline or aniline derivative in a water solution in the approximate range of 0.02 to 0.09 Molar and an ethanol of at least approximately 35 percent of the water solution to permit rapid drying using a slow rate heating profile. Test results may be obtained using a wider tolerance of elements in the first reagent fluid, but there may be reduced detection sensitivity. The titanium metal oxide salt complex and aniline or aniline derivative in water or water ethanol solution is formulated to be shelf stable and procedurally may be used if a first reagent solution is needed to detect peroxide, peroxy-compounds such as HMTD and TATP, and chlorate. Also, other alcohols or blends of alcohols may be used in place of ethanol; however, for example, methanol may be toxic to the user and isopropyl may be less toxic, but may have poorer detection sensitivity results and cause shorter shelf life for the reagent fluid.

Tetrabutylammonium hydroxide may be used in a first or second reagent test to impart a color to nitroaromatic compounds that may otherwise not be detected by other bases, such as, sodium hydroxide or potassium hydroxide regardless of their respective concentrations. The tetrabutylammonium hydroxide may also be strong enough to create nitrite salts from other types of explosives that may be in the test sample in preparation for testing with a second or third type reagent. Use of tetrabutylammonium hydroxide may be difficult due to limited shelf life and its reaction to environmental carbon dioxide that may degrade the necessary color chemistry with nitroaromatics. To develop a solvent system mixable with water to inhibit degradation and reduce hazardous effects to a user, an ethanol and water mixture may be used to inhibit tetrabutylammonium hydroxide degradation with the ethanol ratio such as not to be flammable. The tetrabutylammonium hydroxide concentration may be selected to avoid a reaction with the ethanol. The ethanol and water may also have minimum nitrite content to avoid reaction to a second type reagent test that may give false positive results. For example, if a 10 nanogram detection threshold may be used any nitrite content in the solutions may be less than 0.2 nanograms per microliter of fluid to minimize corruption of test results or false detection.

The first or second reagent test may use a first or second reagent fluid that may have an optimum detection performance range with the fluid having a tetrabutylammonium hydroxide in a water solution. Test results may be obtained using a wide tolerance of elements in the reagent fluid, but there may be reduced detection sensitivity. The tetrabutylammonium hydroxide in a water and ethanol solution is formulated to be shelf life stable and is procedurally used to either counteract the acidity of the first reagent solution if used in the procedure. The tetrabutylammonium hydroxide in water solution may also be used as the first detection reagent solution in the procedure. The tetrabutylammonium hydroxide in water solution is used with a precision heat and time profile to homogenize the reaction conditions of unknown sample types to produce consistent results. The tetrabutylammonium hydroxide in water solution is used to detect certain explosives and prepare other explosives for later detection using a modified procedure commonly known as the Griess reaction. The tetrabutylammonium hydroxide in water solution may be in the approximate range of 0.1 to 1.53 Molar and the ethanol as approximately 5 to 95 percent of the water solution. Also, other alcohols or blends of alcohols may be used in place of ethanol; however, for example, methanol may be toxic to the user and isopropyl may be less toxic, but may have poorer detection sensitivity results and cause shorter shelf life for the reagent fluid.

A second or third reagent test may be a modified Griess reagent test applied after the preparation step with tetrabutylammonium hydroxide under specific reaction conditions of the amount of the reagent, the time of the reaction, the type of surface substrate on which the reaction is carried, the amount of surface area, and the use of uniform and controlled heat. The modified Griess reagent may cause a highly colored azo dye to be created in a reaction with nitrite salts generated in the previous test. The acid that may be used in the formulation of the second or third reagent fluid may be phosphoric acid that may reduce hazardous effects to a user that may become a buffer during the reaction thereby buffering against itself to inhibit creation of too much acid on the swipe pad 42. Other types of acids that may be used in the Griess test may react too violently with the base, may be toxic or hazardous, or may create a strong odor.

The phosphoric acid may be mixed with a solvent that may include but not be limited to water, and with sulfanilic acid and N-(1-naphthyl) ethylenediamine dihydrochloride. The sulfanilic acid may be water soluble with reduced toxicity and it may impart a light magenta to deep fuchsia-purple color to the test sample depending on the type of sample for ease of detection of explosives. N-(1-naphthyl)ethylenediamine dihydrochloride may be water soluble and not carcinogenic as with other salts, and may impart a light magenta to deep fuchsia-purple color to the test sample depending on the type of sample. The second or third reagent solution may use but not be limited to deionized water that may have minimum nitrite content to reduce false positive test results. For example, if a 10 nanogram detection threshold may be used any nitrite content in the solutions may be less than 0.2 nanograms per microliter of fluid to minimize corruption of test results or false detection.

The second or third reagent test may use a second or third reagent fluid that may have an optimum detection performance range with the fluid having a phosphoric acid in a water solution. Test results may be obtained using a wide tolerance of elements in the second or third reagent fluid, but there may be reduced detection sensitivity. The phosphoric acid in water solution may be in the approximate range of 0.1 to 7.35 Molar, the sulfanilic acid may be in the approximate range of 5 to 8 grams, and the N-(1-naphthyl) ethylenediamine dihydrochloride may be in the approximate range of 5 to 9 grams. Other acids, acid combinations, or acid concentrations may be used, but may produce less than optimal testing sensitivity results. Other solutions may have increased acidity and be hazardous to the user as well as have a detrimental effect on the testing device. Other solutions may not be acidic enough for a detection reaction to occur or may be toxic. Other salts may be used, but they may reduce the explosives detection sensitivity.

There may be indicators and a heater switch 100 for use in facilitating the testing of a test sample. An example configuration may be described in an example test method that may be used to test for explosives and related energetic decomposition products as follow. The method used in the procedures for detection may in some cases produce similar colors, but the types of explosives and related energetic decomposition products detected can be resolved from each other by the temperature and time methodology of the procedure.

To perform a test for trace or bulk explosives, the following method may be followed:

1. Open the cover 14 of the testing device 10.
2. Choose to operate either off of the internal batteries or connect the power supply option to run the testing device 10, using either 2.5 mm AC to DC power cord, or a 2.5 mm 12V DC cigarette lighter power cord.
3. Lift up the sample retainer 32.
4. Switch power to ON by sliding the power switch 24 until the green power LED 108 illuminates. If the green LED 108 flashes, replace the 6 AA lithium batteries.
5. A blank swipe pad 42 should be run prior to analysis below. Pull one sample element 40 from the storage bin 70 and tear off at the perforation. Grasp the sample element 40 by the tab end and take care not to bring the circular swipe pad 42 into contact with anything.
6. Insert and secure the "BLANK" sample element 40 so the "CSI" mark is towards the operator. Place the swipe pad 42 in the center using "lock and key" fit to orient the swipe pad 42 fully. Close the sample retainer 32 completely. The yellow LED 102 will begin to flash.
7. If any color changes occur after following steps 11-13 as shown in the Quick Reference Color Chart 80, a positive result is present. Clean hands or swipe retainer 32 area.
8. Pull another sample element 40 from the storage bin 70 and tear off at the perforation. Grasp the sample element 40 by the tab end and take care not to bring the circular cloth swipe pad 42 into contact with anything other than the surface to be tested. Then swipe the cloth pad side of the swipe pad 42 on the surface of interest. Pressing the thumb on the backside of the swipe pad 42 in the area behind the pad helps to apply pressure when swiping. It is not necessary to apply very heavy pressure to the swipe pad 42 to collect particles for testing. This will ensure that nothing other than particulates from the target surface are collected.
9. Insert and secure the sample element 40 so the "CSI" mark is towards the operator. Place the swipe pad 42 in the center using "lock and key" fit to orient the swipe pad 42 fully. Close the sample retainer 32 completely. The yellow LED 102 will begin to flash.

10. If any color changes occur after following steps 11-13 as shown in the Quick Reference Color Chart 80, a positive result is present. Follow appropriate agency guidelines for securing the threat and for securing evidence (including the swipe).

11. Peroxide, HMTD, TATP, and Chlorate Test: The yellow LED 102 flashes for 3 seconds and then stays solid, indicating that it is time to apply a single drop of a first reagent fluid 72 to the center of the swipe pad 42. Apply one drop from the yellow capped container 54 to the swipe pad 42 and then cap and replace container 54 back into its respective cavity. If peroxides are present, a yellow to gold color will instantly appear on the swipe pad 42 depending on the amount present. Press and release the flashing red heater switch 100. The red heater switch 100 will remain on after pressed. The yellow LED 102 will also remain on during this first heat cycle. Within a few seconds, HMTD will appear, if it is present, appearing as a yellow to gold color depending on the amount. About 10 to 18 seconds later, TATP will begin to appear, if present, as a yellow to gold color depending on the amount. Also, if chlorates are on the swipe pad 42, a deep blue color will appear during the same time frame as TATP. The time and colors indicate the type of explosive. Note: The chlorate and/or TATP continue to develop to full color up to 5 seconds after the 13 second heat cycle and when the yellow LED 102 and red heater switch 100 turn off. Do not add the second reagent fluid 74 until the swipe pad 42 is fully evaluated for color.

12. TNT Test: The blue LED 104 flashes for 3 seconds and then stays solid, indicating it is time to apply a single drop of the second reagent fluid 74 to the center of the swipe pad 42. Apply one drop from the blue capped container 56 to the swipe pad 42 and then cap and replace the container 56 back into its respective cavity. Press and release the flashing red heater switch 100. The red heater switch 100 will remain on after pressed. The blue LED 104 will also remain on during this second heat cycle. If TNT is present, a brick red to maroon color will appear instantly after depositing the second reagent fluid 74 or will appear sometime during the second heat cycle, depending on the amount and age of the TNT. Note: some gun propellants have different combinations of DNT isomers. A green blue to blue color indicates DNT is present.

13. High Explosives and Nitrate Test: The red LED 106 flashes for 3 seconds and then stays solid, indicating it is time to apply a single drop of the third reagent fluid 76 to the center of the swipe pad 42. Apply one drop from the red capped container 58 to the swipe pad 42 immediately after the blue LED 106 and heater switch 100 lights turn off and then cap and replace container 58 back into its respective cavity 50. Press and release the flashing red heater button. The red heater switch 100 will continue to remain on after pressed. The red LED 106 will also remain on during the entire third heat cycle. If high explosives are present, a very distinct fuchsia color will appear instantaneously or within a 5 second time frame after dispensing the third reagent fluid 76. Nitrates are detected towards the end of the $3^{rd}$ heat cycle and up to 5 seconds past this heat cycle, appearing as a deeper fuchsia color. Note: Some explosives such as Comp. B will give a positive for TNT followed by a positive for high explosives. Also, continue review of the swipe pad 42 while it is on the heater for up to 5 seconds after the last heat cycle.

14. Lift the sample retainer 32, remove and discard the sample or archive the element 40, and proceed to the next test or power off and store the testing device 10.

While the invention has been particularly shown and described with respect to the illustrated embodiments thereof, it will be understood by those skilled in the art that the foregoing and other changes in form and details may be made therein without departing from the spirit and scope of the invention.

I claim:
1. A method for detecting the presence of explosive elements comprising:
   a) swiping an object to obtain a test sample using a sample element having a swipe pad;
   b) positioning said sample element in a sample holder in a testing device and retaining said sample element with a sample retainer;
   c) applying a first reagent fluid from a fluid container on said swipe pad, the first reagent being a mixture of a titanium metal oxide salt complex, one of an aniline or aniline derivative in a water solution, and ethanol;
   d) evaluating said swipe pad for yellow color indicating peroxide;
   e) activating a heater disposed under said sample element programmed to raise said swipe pad from approximately a temperature of 35 degrees to 115 degrees centigrade;
   f) evaluating said swipe pad for yellow color intensity indicating HMTD or TATP;
   g) evaluating said swipe pad for blue color indicating chlorate;
   h) applying a second reagent fluid from a fluid container on said swipe pad, the second reagent being a mixture of tetrabutylammonium hydroxide and ethanol and water;
   i) activating said heater programmed to raise said swipe pad from approximately 115 degrees centigrade to approximately 135 degrees centigrade and maintaining the temperature for at least approximately 6 to 8 seconds;
   j) evaluating said swipe pad for yellow-orange color for tetryl, blue hue colors for DNT and DNB, and brick red for TNT;
   k) activating said heater programmed to raise said swipe pad from approximately 135 degrees centigrade to approximately 165 degrees centigrade;
   l) applying a third reagent fluid from a fluid container on said swipe pad, the third reagent being a mixture of phosphoric acid, sulfanilic acid, N-(1-naphthyl)ethylenediamine dihydrochloride and a solvent; and
   m) evaluating said swipe pad for purple-fuchsia hue for HME/HE nitrates-nitrites, and for sugar.

2. The method as in claim 1 further comprising:
   applying said first reagent fluid in (c) takes approximately 2.5 seconds;
   evaluating said swipe pad in (d) is completed in approximately 1.5 seconds after (c);
   activating said heater in (e) at approximately 1.5 seconds after (c);
   evaluating said swipe pad in (f) is complete in approximately 2.0 seconds after (e);
   evaluating said swipe pad in (g) is complete between approximately 3.5 and 5.0 seconds after (f);
   applying said second reagent fluid in (h) 8.5 seconds after (c) takes approximately 2.5 seconds;
   activating said heater in (i) at approximately 11.0 seconds after (c);
   evaluating said swipe pad in (j) is complete in approximately 19.5 seconds after (c);
   activating said heater in (k) at approximately 20.5 seconds after (c);

applying said third reagent fluid in (l) 22.5 seconds after (c) takes approximately 2.5 seconds; and evaluating said swipe pad in (m) is complete in approximately 36.5 seconds after (c).

3. The method as in claim 1 wherein said sample holder and said sample retainer retain said sample element to minimize air space between said swipe pad and said heater.

4. The method as in claim 1 wherein said swipe pad is bowed to present a convex surface for disposal against said heater when retained in said sample holder.

5. The method as in claim 1 wherein said testing device has three sequence lights wherein:

a first sequence light flashes when said sample element is retained in said sample holder and transitions to steady illumination after 3.0 seconds;

a second sequence light flashes after said a first heating completes and transitions to steady illumination after 3.0 seconds;

a third sequence light flashes after a second heating completes and transitions to steady illumination after 3.0 seconds.

6. The method as in claim 1 wherein said testing device has a light emitting heater switch wherein said heater switch is programmed to flash to signal push to start for each of three heating cycles for said heater.

7. The method as in claim 1 wherein said heater is programmed to pause in the temperature rise in (e) at a temperature of approximately 55 degrees centigrade for approximately 1.0 second.

8. The method as in claim 1 wherein:

said titanium metal oxide salt complex and said one of said aniline or said aniline derivative in said water solution are in the approximate range of 0.02 to 0.09 Molar; and said ethanol is at least approximately 35 percent of said water solution.

9. The method as in claim 1 wherein said tetrabutylammonium hydroxide in said water solution is in the approximate range of 0.1 to 1.53 Molar, and said ethanol is between approximately 5 and 95 percent of said water solution.

10. The method as in claim 1 wherein:

said phosphoric acid is in a water solution in the approximate range of 0.1 to 7.35 Molar; and said sulfanilic acid is approximately 5 to 8 grams mixed with said N-(1-naphthyl)ethylenediamine dihydrochloride of approximately 5 to 9 grams per 1000 milliliters of said phosphoric acid in said water solution.

* * * * *